United States Patent [19]

Lazzeri et al.

[11] Patent Number: 4,716,894

[45] Date of Patent: Jan. 5, 1988

[54] ACETABULAR CUP INSERTING INSTRUMENT

[75] Inventors: Mark A. Lazzeri; John E. Hamm, both of Warsaw, Ind.

[73] Assignee: Zimmer, Inc., Warsaw, Ind.

[21] Appl. No.: 900,869

[22] Filed: Aug. 27, 1986

[51] Int. Cl.⁴ ............................................... A61F 5/04
[52] U.S. Cl. ................................ 128/92 V; 128/92 VP
[58] Field of Search ............ 128/92 V, 92 VT, 92 VP, 128/92 VL

[56] References Cited

U.S. PATENT DOCUMENTS

| | | | |
|---|---|---|---|
| 3,781,918 | 1/1974 | Mathys | 3/1 |
| 3,859,992 | 1/1975 | Amstutz | 128/92 E |
| 4,305,394 | 12/1981 | Bertuch, Jr. | 128/303 R |
| 4,475,549 | 10/1984 | Oh | 128/303 R |
| 4,528,980 | 7/1985 | Kenna | 128/92 EB |
| 4,632,111 | 12/1986 | Roche | 128/92 V |

OTHER PUBLICATIONS

Zimmer, Inc.—BIAS Acetabular Component-1986.
Zimmer, Inc.—STH-2 Hip-4067-01 Cup Holder-1982.
Zimmer, Inc.—1981 Catalog—pp. A-17, 18, 23, 62, and 70—Various Acetabular Cup Holding/Positioning Instruments.
Zimmer, Inc.—Harris/Galante Porous Hip System Surgical Technique—Cup Positioner of FIG. 17—pp. 16/18—1984.
Zimmer, Inc.—Harris Precoat Hip System Surgical Technique—Cup Positioner of FIG. 16—pp. 12/14—1984.
Howmedica, Inc.-Surgical Techniques: Advances in Total Hip Replacement-Wm. H. Harris, M.D.-Cup Positioner of FIGS. 11/14—pp. 10, 11, 19, 27-No date avail.
Howmedica, Inc.-Surgical Techniques: The Exeter Total Hip System-Ling/Lee—Acetabular Cup Introducer of FIGS. 12 and 13—pp. 4/5—No date available.
Howmedica, Inc.-PCA Total Hip System-Acetabular Alignment Guide on pp. 16, 32, 34, 35, 37-No date available.
Hennepin Country Medical Center, publication on BIAS Total Hip System Surgical Technique—1985—pp. 11/12—Acetabular Driver of FIGS. 14 and 15.

Primary Examiner—C. Fred Rosenbaum
Assistant Examiner—C. W. Shedd
Attorney, Agent, or Firm—Margaret L. Geringer

[57] ABSTRACT

An acetabular cup inserting instrument comprises a first handle and a second handle extending therefrom. The second handle is selectively rotatable about the first handle and selectively lockable in a desired position with respect to the first handle.

15 Claims, 7 Drawing Figures

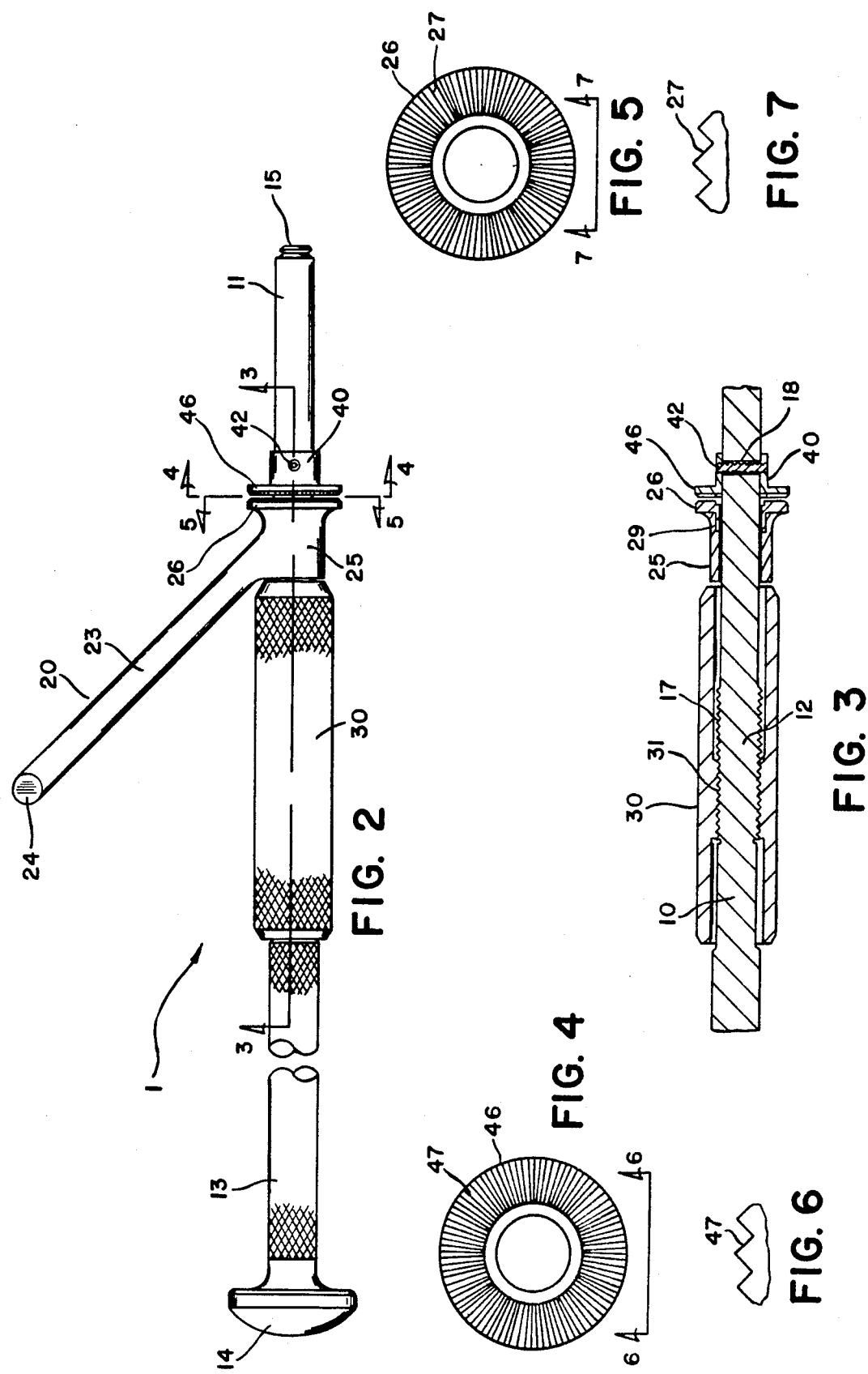

ACETABULAR CUP INSERTING INSTRUMENT

BACKGROUND OF THE INVENTION

The present invention relates to an acetabular cup inserting instrument which is used by a surgeon to insert and properly position an acetabular cup implant into its proper anatomic location.

A wide variety of instruments are known in the art for inserting acetabular cup implants into position in the acetabulum. Many such insertion instruments include a first handle with a second handle extending therefrom to assist in the insertion procedure. Typically, the second handle is in a fixed orientation relative to the first handle. Examples of such acetabular instruments are disclosed in the following U.S. Pats. Nos. 4,528,980 to Kenna; U.S. Pat. No. 4,475,549 to Oh; U.S. Pat. No. 4,305,394 to Bertuch, Jr.; and U.S. Pat. No. 3,859,992 to Amstutz. Once the acetabular cup is attached to such instruments, the handles are in a fixed orientation with regard to the cup. With certain cup designs a particular orientation of the cup may be desirable to achieve proper anatomic positioning. An example of such a cup design is a cup which has pegs protruding from the outer surface, such as the pegged cup disclosed in U.S. Pat. No. 3,781,918 to Mathys or the BIAS Acetabular Cup Component sold by Zimmer, Inc. Accordingly, when the first and second handles are both in a permanently fixed orientation with regard to the cup, it may result in the second handle being in an awkward or inconvenient position in order to insert the cup in the desired orientation. Also, if the first handle needs to be rotated about its axis during the insertion of the cup or the removal of the insertion instrument from the cup, a fixed secondary handle may be awkward or get in the way.

OBJECTS OF THE INVENTION

It is an object of the invention to provide an acetabular cup inserting instrument which has a second handle which is rotatable about the first handle and selectively lockable in a desired position with respect to the first handle.

It is a further object of the invention to provide a simple and reliable securing means for selectively locking the second handle in the desired position.

SUMMARY OF THE INVENTION

The present invention teaches a simple, reliable means for selectively locking a second handle in a desired position with respect to the first handle of an acetabular cup positioning instrument. Accordingly, the present inventions covers an acetabular cup inserting instrument comprising a first elongated handle and a second elongated handle extending therefrom. The second handle is capable of being rotated 360° about the axis of the first elongated handle. The second handle may be selectively locked in a desired position which respect to the first handle via a securing means. The instrument aids in properly positioning an acetabular cup in the acetabulum.

BRIEF DESCRIPTION OF THE DRAWINGS

In the drawings accompanying this application.

FIG. 2 is a side view of the assembled instrument of FIG. 1.

FIG. 3 is a cross-sectional view of the instrument taken along lines 3—3 of FIG. 2.

FIG. 4 is an end view of part 46 taken along lines 4—4 of FIG. 2.

FIG. 5 is an end view of part 26 taken along lines 5—5 of FIG. 2.

FIG. 6 is an enlarged partial edge view taken along lines 6—6 of FIG. 4.

FIG. 7 is an enlarged partial edge view taken along lines 7—7 of FIG. 5.

DETAILED DESCRIPTION OF THE INVENTION

Figure 1:
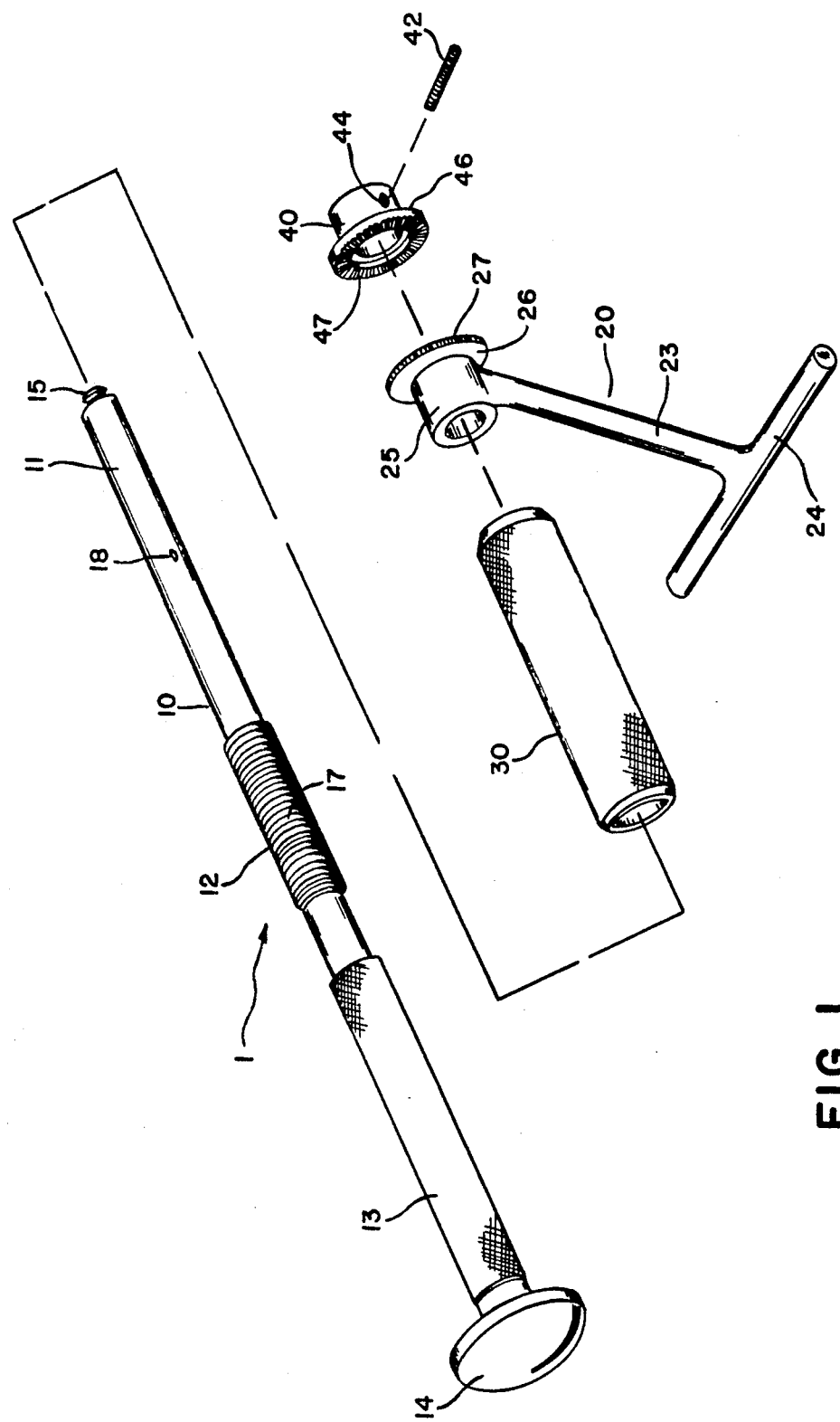
FIG. 1 is an exploded view of the acetabular cup inserting instrument of the present invention.

FIGS. 1-7 illustrate a particularly advantageous embodiment of an acetabular cup inserting instrument according to the present invention.

The acetabular cup inserting instrument 1 includes a first elongated handle 10 and a second elongated handle 20 extending from the first handle 10. The second handle 20 is able to be rotated 360° about the longitudinal axis of the first handle 10. The second handle 20 may be selectively locked at a desired position with respect to the first handle 10.

The first elongated handle 10 includes a distal end 11, a proximal end 13 and an interconnecting intermediate section 12 therebetween. The distal end 11 includes a means for engaging an acetabular cup in order to securely hold it for appropriate positioning. An appropriate means for engaging a cup may be a threaded stud 15 extending from the distal end 11 of the first handle 10. The threaded stud 15 engages a corresponding threaded hole in the acetabular cup (not shown) which is being inserted. A threaded hole in the cup is a particularly suitable attachment means for use with a metal backed cup (well known in the art) in which the separate metal shell of the cup includes the threaded hole for insertion of the shell, and then the separate polyethylene liner is inserted into the shell after the metal shell is in place in the acetabulum. An example of such a metal backed cup is the BIAS Acetabular Cup sold by Zimmer, Inc. However, for the purposes of this invention, whether the instrument is attached to the cup assembly or a cup component, such as a metal shell, it will still be generally referred to as the acetabular cup for simplification and generalization. It is understood that the instrument 1 of this invention may utilize any suitable cup engaging means for securing the instrument 1 to an acetabular cup.

The first handle 10 is provided with an enlarged head 14 rigidly affixed to the proximal end 13. The enlarged head or knob 14 facilitates driving and extraction of the acetabular cup. Also, the proximal end 13 may include a knurled surface as shown in FIGS. 1 and 2 to assist in better gripping of the instrument 1.

The second elongated handle 20 extends from the first elongated handle 10 toward the proximal end 13 of the first handle 10 at an angle of approximately 45° to the first handle 10 as shown in FIG. 2. The second handle 20 includes a main alignment arm extension 23 with a cross bar 24 to form a T-shaped handle. The second handle 20 further includes a first sleeve 25 at the end opposite the cross bar 24. The first sleeve 25 is adapted to fit about the first handle 10 for interconnecting the second handle 20 to the first handle 10. The first sleeve 25 is adapted to be rotatable 360° about the first handle 10.

The instrument 1 further includes a separate second sleeve 40 which is located distally to the first sleeve 25. The second sleeve 40 is adapted to fit about the first handle 10 and is rigidly fixed thereto. The second sleeve 40 may include a threaded hole 44 for accepting a threaded pin 42. The hole 44 is aligned with a threaded hole 18 in the first handle 10 to enable pin 42 to be threaded through holes 44 and 18, thus securing the second sleeve 40 to the first handle 10 in a fixed location.

The instrument 1 includes a securing means to selectively lock the second handle 20 in the desired position with respect to the first handle 10. The first sleeve 25 is freely rotatable about the first handle 10 when the securing means is not operatively locking the second handle in the desired position. The securing means includes a first radial disc 26, a second radial disc 46 and a locking third sleeve 30. The first radial disc 26 extends from the end of the first sleeve 25 closest to the distal end 11 of the first handle 10. The first radial disc 26 may be formed as a separate piece from the first sleeve 25 as shown in FIG. 3. The disc 26 may be integrally formed with a fourth sleeve 29 which may be friction fitted into the inner diameter of first sleeve 25 to fixedly secure first disc 26 to first sleeve 25. The inner diameters of the first sleeve 25 and fourth sleeve 29 are larger than the outer diameter of the first handle 10 to allow the assembly of sleeves 25 and 29 and attached alignment arm 23 to rotate as a unit 360° about the axis of the first handle 10.

The second radial disc 46 extends from the end of the second sleeve 40 closest to the proximal end 13 of the first handle 10 and facing toward the first radial disc 26. The first disc 26 includes a splined surface 27 facing toward the second disc 46 which includes a mating splined surface 47 facing toward the splined surface 27 of the first disc 26. The splined surfaces 27 and 47, as shown in FIGS. 4–7, include a series of projections and grooves on one surface which fit into corresponding grooves and projections on the other surface, such that when the surfaces are matingly fitted and held together, they are interlocked to each other. The splined surfaces 27 and 47 are radially uniform as shown in FIGS. 4 and 5 to enable the surfaces to mate at any selected radial orientation about the longitudinal axis of the first handle 10. Numerous selected positions are available depending upon the number of grooves and projections on each splined surface 27 and 47.

The locking third sleeve 30 is a suitable means for selectively applying a force to maintain the splined surfaces 27 and 47 in locking engagement, thus fixing the second handle 20 in the desired position with respect to the first handle 10 when in locking engagement and enabling the second handle 20 to freely rotate about the first handle 10 when not in locking engagement. The locking third sleeve 30 is adapted to fit about the first handle 10 and is located proximally of the first sleeve 10. The first handle 10 includes external threads 17 on a portion thereof and the third sleeve 30 includes mating internal threads 31 on its inner diameter for threaded engagement with the external threads 17 to enable the position of the third sleeve 30 to be manually controlled via rotation of the third sleeve 30 along the threaded area 17 on the first handle 10. The locking third sleeve 30 may be rotated into selective contact with the rotatable first sleeve 25, thus applying force against the first sleeve 25 to maintain or force the splined surfaces 27 and 47 into mating and locking engagement with one another, thus fixing the position of the second handle 20. The third sleeve 30 may also be selectively manually rotated out of contact with the first sleeve 25 and retracted toward the proximal end 13 of the first handle 10, thus releasing the force against the first sleeve 25 of the second handle 20 to enable the second handle 20 the freedom of movement to disengage the splined surfaces 27 and 47, thus enabling the second handle 20 the ability to freely rotate about the first handle 10. The third sleeve 30 may include a knurled surface as shown in FIGS. 1 and 2 to assist in better gripping of the third sleeve 30.

In order to utilize the instrument 1 of the present invention, the instrument 1 is attached to an acetabular cup (not shown). In the embodiment illustrated, this entails threading the stud 15 into a corresponding threaded hole in an acetabular cup. The stud 15 should be fully threaded onto the acetabular cup, so that the first handle 10 and not the threads of the stud 15 bear the load during impaction or insertion of the cup. Thereafter, the second handle 20 is rotated to the desired position with respect to the first handle 10. The locking sleeve 30 is rotated into engagement with first sleeve 25 to apply the force necessary to maintain the splined surfaces 27 and 47 in engagement with each other, thus locking or fixing the position of the second handle 20. The cup is properly aligned in the desired proper anatomic position, and the cup is then properly positioned and inserted into the prepared acetabulum. When the acetabular cup is fully seated in the acetabulum, the third locking sleeve 30 is retracted to release the securing means, so that the second handle 20 is again free to rotate about the first handle 10. The instrument 1 is then removed from the acetabular cup by unthreading the stud 15 from the cup.

It can be readily seen that the present invention provides a second alignment handle 20 which can be rotated 360° about the axis of the elongated first handle 10 and then selectively locked in a desired position. The invention provides a simple and effective instrument which aids in the proper insertion of acetabular cup implants. While this invention has been described and exemplified in terms of a particularly advantageous embodiment, those skilled in the art can appreciate that modifications can be made without departing from the spirit and scope of this invention.

We claim:

1. An acetabular cup inserting instrument comprising a first elongated handle and a second elongated handle extending from the first handle, the second handle being selectively rotatable about the first handle and selectively lockable in a desired position with respect to the first handle, and wherein the first elongated handle includes a proximal end, a distal end and an interconnecting intermediate section therebetween.

2. The instrument of claim 1 wherein the second handle includes a first sleeve adapted to fit about the first handle for interconnecting the second handle to the first handle, the instrument including a securing means to selectively lock the second handle in the desired position with respect to the first handle, and the first sleeve being freely rotatable about the first handle when the securing means is not operatively locking the second handle in the desired position.

3. The instrument of claim 2 wherein the instrument further includes a second sleeve which is located distally to the first sleeve, the second sleeve is adapted to fit about the first handle and is rigidly fixed thereto, and wherein the securing means includes a first radial disc extending from the end of the first sleeve closest to the distal end of the first handle and a second radial disc extending from the end of the second sleeve closest to the proximal end thereof and facing toward the first radial disc, the first disc includes a splined surface facing toward the second disc, and the second disc includes a mating splined surface facing toward the splined surface of the first disc, the securing means further including a locking means to selectively maintain the splined surfaces in locking engagement, thus fixing the second handle in the desired position with respect to the first handle when the locking means is effecting locking engagement, and enabling the second handle to freely rotate about the first handle when the locking means is not effecting locking engagement.

4. The instrument of claim 3 wherein the locking means to selectively maintain the splined surfaces in locking engagement is a third sleeve member adapted to fit about the first handle and located proximally to the first sleeve, the first handle including external threads on a portion thereof and the third sleeve including mating internal threads for engagement with the external threads to enable the third sleeve to be manually rotated about the first handle via the threaded engagement into selective contact with the first sleeve, thus applying force against the first sleeve to maintain the mating splined surfaces in engagement with one another, thereby fixing the position of the second handle, the third sleeve may also be selectively manually rotated out of contact with the first sleeve and retracted toward the proximal end of the first handle, thus releasing the force against the first sleeve of the second handle to enable the second handle the freedom of movement to disengage the splined surfaces, thus enabling the second handle the ability to freely rotate about the first handle.

5. The instrument of claim 1 wherein the second handle is at an angle of approximately 45° to the first handle.

6. The instrument of claim 1 wherein the second handle is a T-shaped handle.

7. The instrument of claim 1 wherein the instrument further includes a means for engaging the acetabular cup.

8. The instrument of claim 7 wherein the means for engaging the acetabular cup is a threaded stud extending from the distal end of the first handle for engaging a corresponding threaded hole in the acetabular cup which is being inserted.

9. The instrument of claim 1 wherein the second handle is selectively rotatable 360° about the first handle.

10. A method of inserting an acetabular cup with an instrument having a first elongated handle and a second elongated handle extending from the first handle, wherein the second handle is selectively rotatable about the first handle and selectively lockable via a securing means in a desired position with respect to the first handle, the method comprising the following steps:
   (a) releasably attaching the instrument to an acetabular cup;
   (b) rotating the second handle about the first handle to the desired position;
   (c) locking the second handle in the desired position via the securing means;
   (d) aligning the cup to the proper anatomic orientation; and
   (e) properly positioning and inserting the cup in the prepared acetabulum.

11. The method of claim 10 further comprising the following additional steps:
   (a) releasing the securing means so that the second handle is free to rotate about the first handle; and
   (b) removing the instrument from the acetabular cup.

12. An acetabular cup inserting instrument comprising a first elongated handle and a second elongated handle extending from the first handle, the second handle being selectively rotatable about the first handle and selectively lockable in a desired position with respect to the first handle, and wherein the first elongated handle includes a proximal end, a distal end and an interconnecting intermediate section therebetween, and wherein the second handle includes a first sleeve adapted to fit about the first handle for interconnecting the second handle to the first handle, the instrument including a securing means to selectively lock the second handle in the desired position with respect to the first handle, and the first sleeve being freely rotatable about the first handle when the securing means is not operatively locking the second handle in the desired position, and wherein the instrument further includes a second sleeve which is located distally to the first sleeve, the second sleeve is adapted to fit about the first handle and is rigidly fixed thereto, and wherein the securing means includes a first radial disc extending from the end of the first sleeve closest to the distal end of the first handle and a second radial disc extending from the end of the second sleeve closest to the proximal end thereof and facing toward the first radial disc, the first disc includes a splined surface facing toward the second disc, and the second disc includes a mating splined surface facing toward the splined surface of the first disc, the securing means further including a locking means to selectively maintain the splined surfaces in locking engagement, thus fixing the second handle in the desired position with respect to the first handle when the locking means is effecting locking engagement, and enabling the second handle to freely rotate about the first handle when the locking means is not effecting locking engagement.

13. An acetabular cup inserting instrument comprising a first elongated handle and a second elongated handle extending from the first handle, the second handle being selectively rotatable about the first handle and selectively lockable in a desired position with respect to the first handle, and wherein the first elongated handle includes a proximal end, a distal end and an interconnecting intermediate section therebetween, and wherein the second handle includes a connecting means adapted to fit about the first handle for interconnecting the second handle to the first handle, the instrument including a securing means to selectively lock the second handle in the desired position with respect to the first handle, and the connecting means being freely rotatable about the first handle when the securing means is not operatively locking the second handle in the desired position.

14. The instrument of claim 13 wherein the securing means includes a first radial disc extending from the connecting means and a second radial disc extending from the first handle and in a fixed relation to the first handle, and facing toward the first radial disc, the first disc includes a splined surface facing toward the second disc, and the second disc includes a mating splined surface facing toward the splined surface of the first disc, the securing means further including a locking means to selectively maintain the splined surfaces in locking engagement, thus fixing the second handle in the desired position with respect to the first handle when the locking means is effecting locking engagement, and enabling the second handle to freely rotate about the first handle when the locking means is not effecting locking engagement.

15. The instrument of claim 13 wherein the securing means includes a projection means selectively engageable with a corresponding groove means with one of these two means being incorporated on the rotatable connecting means and the other being incorporated on the first handle in a fixed radial orientation, thus fixing the second handle in the desired position with respect to the first handle when the projection means is operatively engaged with the groove means, and enabling the second handle to freely rotate about the first handle when the projection means is not operatively engaged with the groove means.

* * * * *